United States Patent [19]
Kaminsky et al.

[11] Patent Number: 5,312,795
[45] Date of Patent: May 17, 1994

[54] HYDROCARBON CONVERSION

[75] Inventors: Mark P. Kaminsky, Winfield; Mark S. Kleefisch, Naperville; George A. Huff, Jr., Naperville; Don M. Washecheck, Naperville; Mark K. Barr, Wheaton, all of Ill.

[73] Assignee: Amoco Corporation, Chicago, Ill.

[21] Appl. No.: 975,280

[22] Filed: Nov. 12, 1992

Related U.S. Application Data

[62] Division of Ser. No. 775,227, Oct. 11, 1991, Pat. No. 5,198,596.

[51] Int. Cl.[5] .............................................. B01J 21/18
[52] U.S. Cl. ................................... 502/174; 502/341; 502/349
[58] Field of Search ..................... 502/174, 341, 349

[56] References Cited

U.S. PATENT DOCUMENTS

| | | | |
|---|---|---|---|
| 3,976,599 | 8/1976 | Whelan | 502/341 |
| 4,780,449 | 10/1988 | Hicks | 502/341 |
| 5,015,617 | 5/1991 | Ohata et al. | 502/349 |

Primary Examiner—Patrick P. Garvin
Assistant Examiner—E. D. Irzinski
Attorney, Agent, or Firm—Scott P. McDonald; James R. Henes; Richard A. Kretchmer

[57] ABSTRACT

A contact material composition containing an intimately mixed, mixed oxide of at least one cationic species of a naturally occurring Group IIIB element, at least one cationic species of a Group IIA metal of magnesium, calcium, strontium, and barium and at least one additional metal cationic species of zirconium and hafnium, as well as methods for hydrocarbon conversion using such contact material compositions are provided.

14 Claims, 4 Drawing Sheets

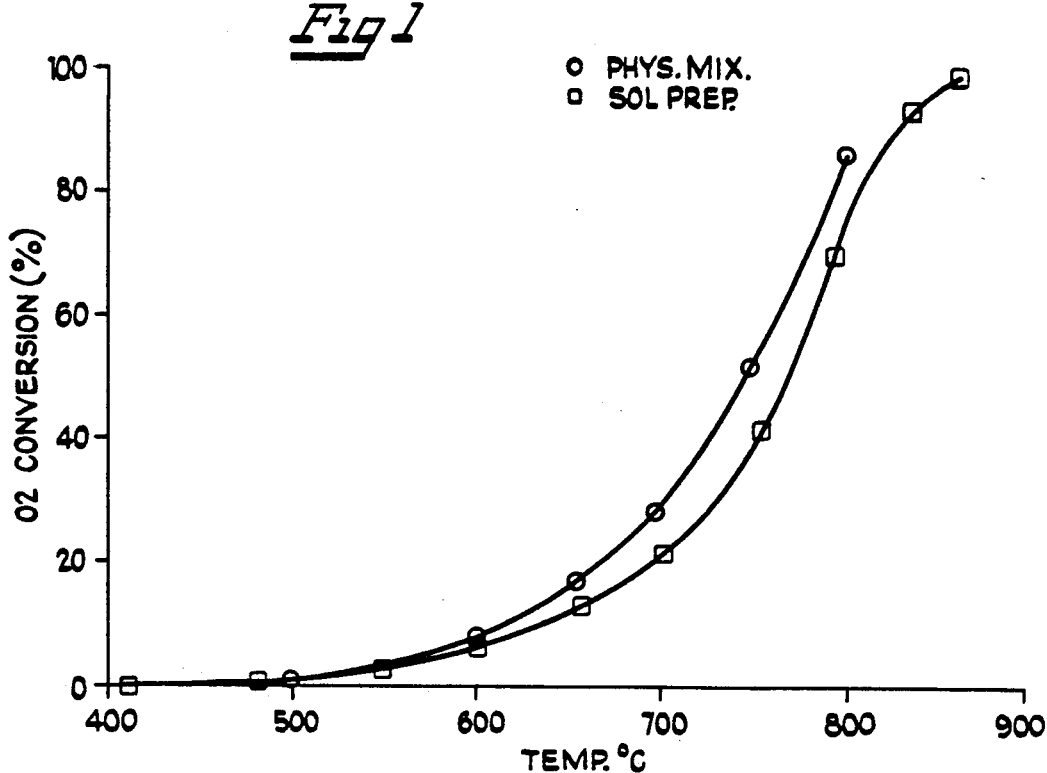
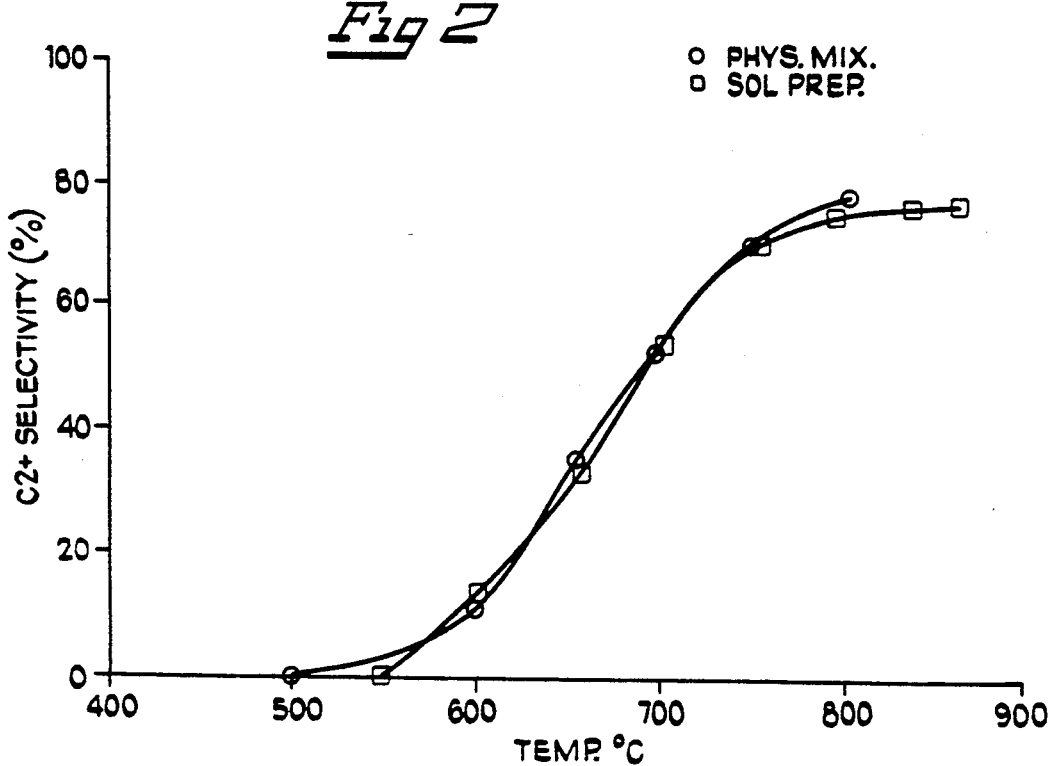

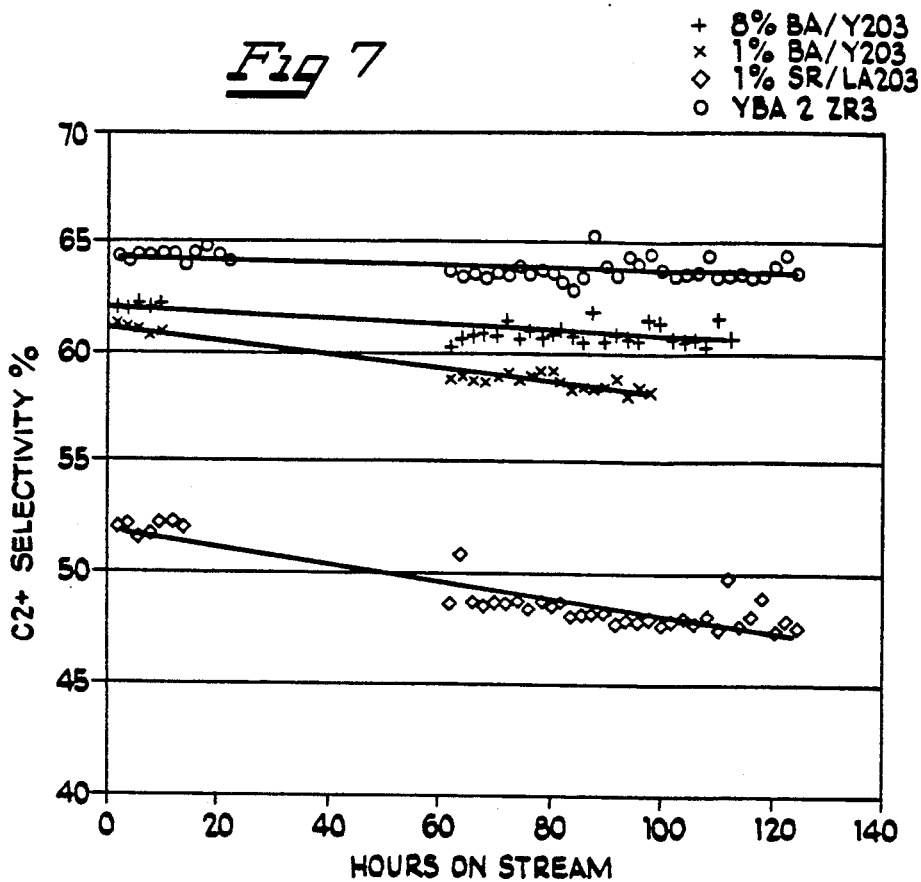
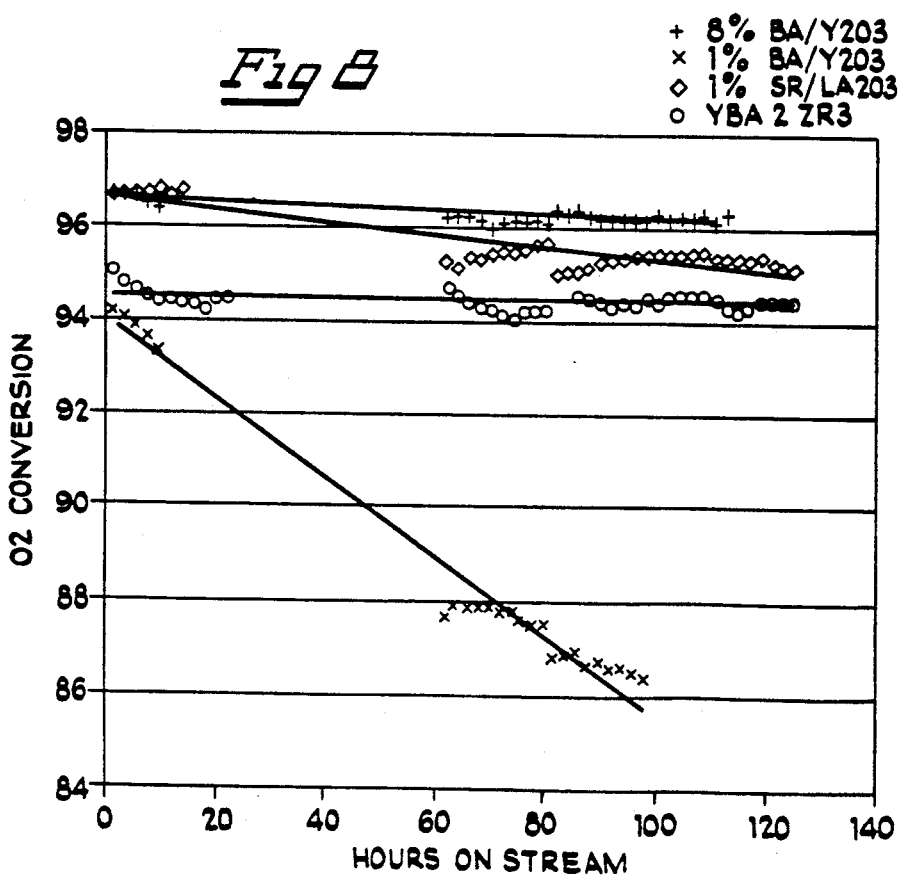

HYDROCARBON CONVERSION

This is a divisional of application Ser. No. 07/775,227, filed Oct. 11, 1991, and now U.S. Pat. No. 5,198,596.

BACKGROUND OF THE INVENTION

This invention relates generally to the conversion of hydrocarbons and, more specifically, to contact material compositions and oxidative conversion processes using such compositions.

As the uncertain nature of the limited supplies of and access to crude oil has become increasingly apparent, alternative sources of hydrocarbons and fuels have been sought out and explored. The conversion of low molecular weight alkanes (lower alkanes) to higher molecular weight hydrocarbons has received increasing consideration as such low molecular weight alkanes may be generally available from more readily secured and reliable sources. Natural gas, partially as a result of its comparative abundance, has received a large measure of the attention that has focused on sources of low molecular weight alkanes. Large deposits of natural gas, mainly composed of methane, are found in many locations throughout the world. In addition, low molecular weight alkanes are generally present in coal deposits and may be formed during numerous mining operations, in various petroleum processes, and in the above- or below-ground gasification or liquefaction of coal, tar sands, oil shale and biomass, for example.

Today, much of the readily accessible natural gas generally has a high valued use as a fuel whether in residential, commercial or in industrial applications. Additional natural gas resources, however, are prevalent in many remote regions of the world, such as remote areas of Western Canada, Africa, Australia, U.S.S.R. and Asia. Commonly, natural gas from these remote resources is referred to as "remote natural gas" or, more briefly, "remote gas."

In many such remote regions, the widespread, direct use of the natural gas as a fuel is generally not currently profitable. Further, the relative inaccessibility of gas from such resources is a major obstacle to the more effective and extensive use of remote gas as the transportation of the gas to distant markets wherein the natural gas could find direct use as a fuel is typically economically unattractive.

Of course, while the primary current use of natural gas is as a fuel, natural gas may alternatively be used as a feedstock for chemical manufacture. In fact, natural gas is a primary chemical feedstock for the manufacture of numerous chemicals, such as methanol, ammonia, acetic acid, acetic anhydride, formic acid, and formaldehyde, for example. However, the markets for such chemicals are fairly limited in size. Consequently, methods for converting low molecular weight alkanes, such as those present in remote natural gas, to higher molecular weight hydrocarbons, preferably, to more easily transportable liquid fuels for which the world market is relatively large and/or elastic, are desired and a number of such methods have been proposed or reported.

Conversion of natural gas to liquid products is a promising solution to the problem of more effectively and efficiently utilizing low molecular weight hydrocarbons from remote areas and constitutes a special challenge to the petrochemical and energy industries. The dominant technology currently employed for the utilization of remote natural gas involves conversion of the natural gas to a liquid form via the formation of synthesis gas, i.e., a process intermediary composed of a mixture of hydrogen and carbon monoxide also commonly referred to as "syngas." In syngas processing, methane, the predominant component of natural gas, although typically difficult to activate, is reacted with oxygen or oxygen-containing compounds such as water or carbon dioxide to produce syngas which in turn is then converted to desired products.

Syngas processing, however, is relatively costly as the production of syngas and the subsequent conversion of the syngas are typically very capital intensive processing schemes. Further, while some of the products to which syngas can be converted, such as methanol, mixed alcohols, acetic acid, etc., contain oxygen and are thus logical products for production via syngas processing, hydrocarbon products such as gasoline and diesel fuel typically do not contain oxygen and consequently the production of such materials via syngas processing requires the additional processing step of oxygen removal. Consequently, when such products are produced via syngas processing, the addition and later removal of oxygen ultimately increases the cost of production.

When hydrocarbon products such as gasoline and diesel fuel are sought, the syngas mixture can be converted to syncrude, such as with Fischer-Tropsch technology, and then upgraded to the desired transportation fuels using typical refining methods. Alternatively, syngas can be converted to liquid oxygenates which can be blended with conventional transportation fuels to form materials such as gasohol, used as an alternative fuel or converted to conventional transportation fuels by catalysts such as certain zeolites.

Because syngas processing typically requires high capital investment, with syngas typically being produced in energy intensive ways such as by steam reforming where fuel is burned to supply the heat of reforming, and represents an indirect means of higher hydrocarbon production (i.e., such processing involves the formation and subsequent reaction of the syngas intermediaries), other means for converting lower alkanes directly to higher hydrocarbons have been sought.

Oxidative coupling has been recognized as a promising approach to the problem of conversion of lower alkanes to higher molecular weight hydrocarbons. The mechanism of action of oxidative coupling processing, however, has not been clearly identified or defined and is not clearly understood. In such oxidative coupling processing, a low molecular weight alkane or a mixture containing low molecular weight alkanes, such as methane, is contacted with a solid material referred to by various terms including catalyst, promoter, oxidative synthesizing agent, activator or contact material. In such processing, the methane is contacted with such a "contact material" and, depending on the composition of the contact material, in the presence or absence of free oxygen gas, is directly converted to ethane, ethylene, higher hydrocarbons and water. Carbon dioxide, the formation of which is highly favored thermodynamically, is an undesired product, however, as the formation of carbon dioxide results in both oxygen and carbon being consumed without production of the desired higher value $C_{2+}$ hydrocarbons.

Catalytic mixtures containing reducible metal oxides are highly active and many are 100% selective for producing $CO_2$, that is, they are combustion catalysts. In order to obtain desired selectivity for hydrocarbon formation, Group IA metals, particularly lithium and sodium, have been used in such catalytic mixtures. Under the conditions used for oxidative coupling, however, migration and loss of the alkali metal normally occurs. In order to avoid complete combustion most methods for oxidative conversion have been carried out in the absence of an oxygen-containing gas, relying on the oxygen theoretically being supplied by the catalyst.

Nevertheless, in most cases involving oxidative coupling processing of methane, carbon monoxide and hydrogen are coproduced in addition to desired $C_{2+}$ hydrocarbons. If desired, such coproduced hydrogen can be used alone, in part or in its entirety, or supplemented with hydrogen from another source to effect conversion of carbon oxides to produce methane. Such produced methane can, in turn, be recycled for desired oxidative coupling processing. Alternatively, the hydrogen can be used to effect conversion of carbon monoxide to carbon-containing oxygenates such as methanol or mixed alcohols (e.g., a mixture of one or more alcohols such as methanol, ethanol, propanols and butanols) or higher hydrocarbons such as a mixture of paraffins and olefins typically produced in the process commonly known as Fischer-Tropsch synthesis. Alternatively or in addition, such coproduced carbon monoxide and hydrogen can, if desired, be combined with olefins, such as those produced during the oxidative coupling processing, to produce various oxygenates, such as propanol, for example. As described above, however, the production of materials such as oxygenates from carbon monoxide and hydrogen (i.e., synthesis gas) is not a direct approach for the utilization of natural gas, as such processing still involves the use of the syngas intermediaries.

Furthermore, the processing of coproduced hydrogen and carbon monoxide typically increases the cost of any such processing scheme. Thus, the need for active oxidative coupling contact materials which have relatively high selectivities for desired higher hydrocarbons and which contact materials are stable and have long life (i.e., maintain relatively high levels of activity and selectivity to higher hydrocarbons over extended periods of use without the need for regeneration or replacement).

Many patents describe processes for converting methane to heavier hydrocarbons in the presence of reducible metal oxide catalysts. During such processing, the reducible metal oxide "catalyst" typically is reduced and thus most of these patents require or imply the need for a separate stage to reoxidize the catalyst.

For example, U.S. Pat. No. 4,444,984 discloses a method for synthesizing hydrocarbons wherein methane is contacted with a reducible oxide of tin at an elevated temperature. Such contact results in the tin oxide being reduced. The reduced composition is then oxidized with molecular oxygen to regenerate a reducible oxide of tin.

U.S. Pat. No. 4,495,374 discloses the use of a reducible metal oxide promoted by an alkaline earth metal in such a method of methane conversion. During such processing, the reducible metal oxide of the promoted oxidative synthesizing agent is reduced. The reduced synthesizing agent can then be removed to a separate zone wherein it is contacted with an oxygen-containing gas to regenerate the promoted oxidative synthesizing agent.

Examples of other such patents include: U.S. Pat. No. 4,523,049, which shows a reducible oxide catalyst promoted by an alkali or alkaline earth metal, and requires the presence of oxygen during the oxidative coupling reaction; U.S. Pat. No. 4,656,155, which specifies a reducible metal oxide in combination with an oxide of zirconium, an oxide of yttrium and, optionally, an alkali metal; U.S. Pat. No. 4,450,310, which is directed to coupling promoted by alkaline earth metal oxides in the total absence of molecular oxygen; and U.S. Pat. No. 4,482,644, which teaches a barium-containing oxygen-deficient catalyst with a perovskite structure.

Several patents describe catalyst for higher hydrocarbon synthesis which can include a Group IIA; a metal of scandium, yttrium or lanthanum; and/or other metal oxides.

Commonly assigned U.S. Pat. No. 4,931,311 discloses a catalyst composition comprising a mixed oxide of:

a) a Group IIIB metal selected from the group consisting of yttrium, scandium and lanthanum;

b) a Group IIA metal selected from the group consisting of barium, calcium and strontium; and c) a Group IVA metal selected from the group consisting of tin, lead and germanium, with the Group IIIB, Group IIA and Group IVA metals in an approximate mole ratio of 1:0.5–3:2–4, respectively.

U.S. Pat. No. 4,780,449 discloses a catalyst including metal oxides of a Group IIA metal, a Group IIIA metal, a lanthanide series metal excluding Ce, or mixtures thereof. The patent lists as optional promoter materials metal oxides of a metal of Groups IA, IIA, IIIA, IVB, VB, IB, the lanthanide series, or mixtures thereof.

Catalysts which contain metal oxides which are reduced under the reaction conditions of use are typically physically and/or chemically relatively unstable under the reaction conditions of use. That is, such catalysts generally do not maintain needed or desired physical and/or chemical characteristics for extended periods of time (e.g., such characteristics as reactivity and physical form are typically not maintained for more than a few minutes) without regeneration, reformation or other remedial procedures.

Also, as the reducible metal oxides of such materials typically undergo chemical reduction with use, the activity of the materials for producing desired products, such as $C_{2+}$ hydrocarbons in the oxidative coupling processing of methane, for example, worsen.

For example, with contact materials containing reducible metal oxides, the problem of over-reduction is typically associated with the reduction of the metal oxide to the metal. Often, the selectivity of the contact material changes dramatically when the material has been over-reduced, leading to a material which results in combustion reactions or which results in the formation of mixtures of carbon oxides with water and hydrogen when the material is used in the oxidative coupling of lower alkanes such as methane, for example. Some reducible metal oxide-containing contact materials (e.g., manganese oxide) at temperatures in the range of about 800° to about 1,000° C. and in the absence of oxygen, once over-reduced are very difficult to reoxidize and a permanent or near permanent alteration in the characteristics of the material occurs. In some cases, the reduced metal can react with other materials in the composition to form a new phase which is difficult to reoxidize and the contact material is permanently damaged by over-reduction. Such alterations can, for example, result in a loss in selectivity to $C_{2+}$ hydrocarbons when the material is used in the oxidative coupling of methane.

Furthermore, contact materials containing metal oxides which are reducible under the reaction conditions of use can, during such use, experience physical deterioration, e.g., breaking apart. Such physical deterioration results, at least in part, from changes in the material during oxidation and reduction. Frequently, the material in its various oxidation states has very different densities, e.g., the material contracts and swells as it is reduced and oxidized. The smaller particles or powders, frequently referred to as "fines," resulting when the material undergoes physical degradation results in pressure drop buildups (in fixed bed operation) and leads to loss of contact material (in fluid bed operation).

In fluid bed operation, fines are frequently carried out with the vapors from the reactor. Additionally, the fines are generally not easily separated from the product gases in common separating devices such as cyclones. Thus, costly separation techniques are required to effect separation of the fines from the product gases. The loss of contact material in the form of fines also necessitates the addition of more contact material to the process to replace that which has been lost and thereby increases the cost of such processing.

The search for a stable, long-lived contact material having high activity and selectivity in the oxidative conversion processing of hydrocarbons has continued.

SUMMARY OF THE INVENTION

The general object of this invention is to provide an improved contact material composition and improved methods for the oxidative conversion of hydrocarbons.

It is an object of the present invention to overcome one or more of the problems described above.

The general object of this invention can be attained, at least in part, through a composition including an intimately mixed, mixed oxide of:

a) at least one cationic species of a naturally occurring Group IIIB element;

b) at least one cationic species of a Group IIA metal of magnesium, calcium, strontium and barium; and c) at least one cationic species of zirconium and hafnium.

The prior art fails to disclose or suggest stable contact material compositions containing an intimately mixed, mixed oxide of these cationic species. The stable contact material compositions of the invention by being able to maintain needed or desired physical and/or chemical characteristics for extended periods of time in use, permit the use thereof in processing without necessitating troublesome and/or costly remedial procedures.

The invention further comprehends a composition including an intimately mixed, mixed oxide of:

a) at least one cationic species of a Group IIIB element selected from the group consisting of yttrium, lanthanum, neodymium, samarium and ytterbium;

b) at least one cationic species of a Group IIA metal of magnesium, calcium, strontium and barium; and c) at least one cationic species of zirconium and hafnium.

The invention still further comprehends a composition including an intimately mixed, mixed oxide of:

a) a cationic species of yttrium;

b) at least one cationic species of a Group IIA metal of strontium and barium; and c) at least one cationic species of zirconium.

The invention also comprehends methods for the conversion of lower alkanes to higher molecular weight hydrocarbons. In such methods, a feed composition including at least one lower alkane species is contacted with the specified contact material composition. Such contacting is done in the presence of oxygen and at oxidative coupling reaction conditions.

The invention also comprehends methods for the oxidative dehydrogenation of dehydrogenatable hydrocarbons. In such methods, oxygen and a gas containing a dehydrogenatable hydrocarbon are contacted with the specified contact material composition at oxidative dehydrogenation reaction conditions to produce an effluent containing dehydrogenated hydrocarbons.

The invention also comprehends methods for the oxidative cracking of crackable hydrocarbons. In such methods, oxygen and a gas containing a crackable hydrocarbon are contacted with the specified contact material composition at oxidative cracking reaction conditions to produce an effluent containing cracked hydrocarbons.

As used herein, the term "reducible" is used to identify those oxides of metals which are reduced by contact with $C_1$-$C_3$ alkanes at temperatures within the range of about 500° C. to about 1,000° C.

The terms "dehydrogenatable hydrocarbons" and "crackable hydrocarbons" include not only conventional hydrocarbons, which contain exclusively hydrogen and carbon, but also compounds, which in addition to hydrogen and carbon, contain oxygen as well, e.g., compounds such as alcohols ($C_{2+}$ and $C_{3+}$ alcohols, for example).

The term "catalytically effective" refers to the ability of the material in question to increase chemical reactivity for the formation of hydrocarbons in preference to carbon oxide (CO and $CO_2$) formation.

The terms "oxide" and "oxides" include the various oxygen-containing compositions including hydroxides, carbonates, peroxides, superoxides and mixtures thereof, for example.

The term "lower alkane" as used herein refers to $C_1$-$C_3$ alkanes.

The term "contact material" as used herein refers to a material which:

(a) when contacted with a lower alkane and oxygen at oxidative coupling reaction conditions results in the formation of hydrocarbons having a higher molecular weight than the original feed alkane, or (b) when contacted with a higher hydrocarbon (e.g., butanes, pentanes, hexanes and mixtures thereof) at oxidative dehydrogenation or oxidative cracking reaction conditions leads to a dehydrogenation and/or molecular weight reduction, respectively, of the higher hydrocarbon, generally with the formation of dehydrogenated lower molecular weight hydrocarbons.

The term "cofeed" operation as used herein refers to that mode of conversion operation wherein the contact material is simultaneously contacted by the feed materials, e.g., feed hydrocarbon, and oxygen (such as in the form of an oxygen-containing gas). In such operation, the feed material and the oxygen can be mixed together before or during their contact with the contact material.

The term "redox" operation as used herein refers to that mode of conversion operation wherein the contact material is sequentially contacted by the feed materials, e.g., feed hydrocarbon, followed by contact with oxygen (such as in the form of an oxygen-containing gas). In such operation, the feed material and oxygen are generally not mixed together to any substantial extent either before or during contact with the contact material. In some process designs, however, some such "carryover" or inadvertent mixing of the feed material and oxygen may occur.

The term "gasoline-type hydrocarbon products" as used herein refers to those hydrocarbons having a boiling point in the general range of $C_4$ hydrocarbons to about 450° F., inclusive.

The term "substantially free" as used herein to describe the contact material composition generally indicates that the contact material composition excludes amounts of the specified material(s) which materially affect the effectiveness of the contact material in the specified processing. While the affect of a specified material on the effectiveness of the contact material will, of course, be dependent on the material and processing involved, "substantially free" means that the contact material composition includes no more than nominal amounts of the specified materials, typically the composition contains an amount of no more than about 0.1 wt %, more specifically the composition contains an amount of no more than about 100 ppm (0.01 wt. %) and more preferably the composition contains an amount of no more than about 50 ppm (0.005 wt. %) of the specified materials.

The term "intimately mixed" as used herein refers to mixing of the different contact material cationic species, either alone or in some compound form, on a molecular level. The term is descriptive of and refers to materials which when thin sectioned to about 90 nanometers or dispersed on a carbon film and scanned over a spot of no more than about 5 to 10 square microns, preferably a spot of no more than about 1 to 5 square microns and, more preferably, a spot of no more than about 0.1 to 1 square micron by way of Scanning Transmission Electron Microscopy with Energy Dispersive X-Ray Analysis (STEM-EDX) exhibits each of the three principal metal cationic species of the material in significant amounts (i.e., more than contaminant or impurity amounts).

Other objects and advantages of the invention will be apparent to those skilled in the art from the following detailed description taken in conjunction with the appended claims and figures.

BRIEF DESCRIPTION OF THE DRAWINGS

FIGS. 1 and 2 are graphical depictions of $O_2$ conversion and $C_{2+}$ selectivity, respectively, versus reaction temperature for conversion of methane to higher molecular weight hydrocarbons according to typical embodiments of the invention.

FIGS. 7 and 8 are graphical depictions of $C_{2+}$ selectivity and $O_2$ conversion, respectively, versus time on stream for conversion of methane to higher molecular weight hydrocarbons according to a typical embodiment of the invention as well as a process utilizing comparative contact materials.

DETAILED DESCRIPTION OF THE INVENTION

Figure 3:
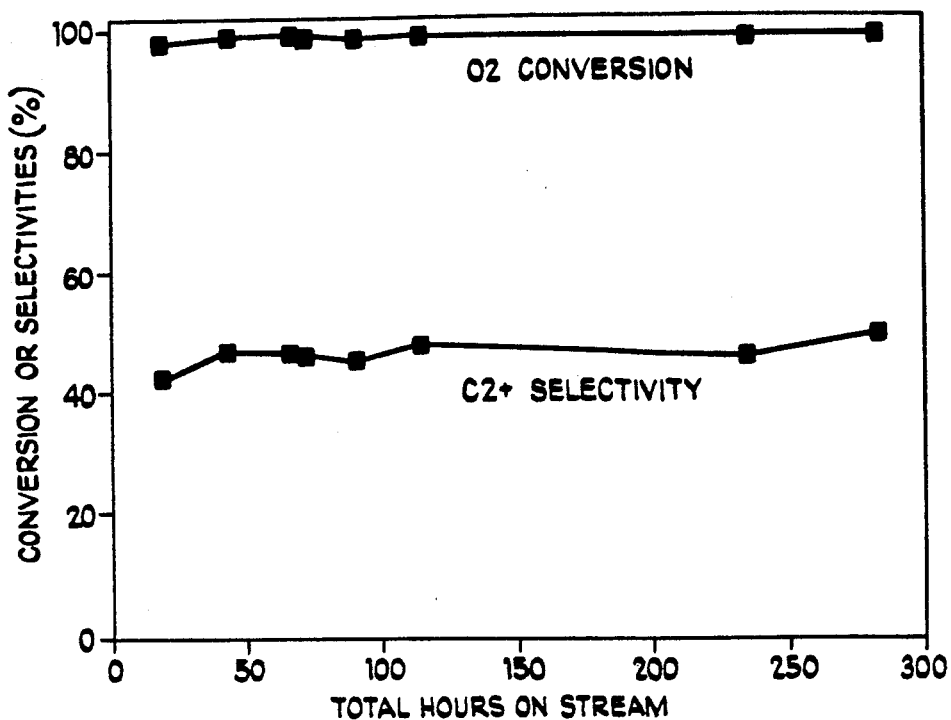
FIGS. 3, 4 and 5 are graphical depictions of $O_2$ conversion and $C_{2+}$ selectivity versus time onstream for conversion of methane to higher molecular weight hydrocarbons according to typical embodiments of the invention.

According to the invention, an oxidative coupling contact material and methods for hydrocarbon conversion are provided. The invention contemplates an oxidative coupling contact material composition which is substantially free of catalytically effective reducible metal oxide and methods of hydrocarbon conversion utilizing such contact material compositions including:

a) methods for alkane conversion generally applicable to alkanes containing from 1 to 3 carbon atoms to form higher molecular weight hydrocarbons, b) methods for dehydrogenation of dehydrogenatable hydrocarbons; and c) methods for the cracking of crackable hydrocarbons.

In one preferred embodiment of the invention, methane, illustrative of a lower molecular weight alkane feedstock useful in the practice of the invention, is mixed with air, as a source of oxygen, and the resulting mixture is contacted with a suitable oxidative coupling contact material, as described below, for the oxidative coupling of the aforesaid alkane. Thus, the invention will be described herein with reference to conversion wherein the lower alkanes converted to higher molecular weight hydrocarbons comprise methane. It is to be understood, however, that feedstocks typically useful in the practice of the invention will include lower alkanes such as methane, ethane or propane (i.e., $C_1$-$C_3$ alkanes) either alone, separately or in mixtures with each other, with or without the presence of other materials, such as inert gases, e.g., $N_2$ or minor amounts of other hydrocarbon materials, for example. Natural gas is an example of a feedstock for use in the practice of at least some aspects of the invention. It being understood that natural gas, while containing predominantly methane, can and typically does contain at least minor amounts of the other above-identified lower alkanes as well as other materials such as nitrogen gas and carbon dioxide, for example. Also, it is to be understood, that the method can be utilized with higher alkane feedstocks. As a result of competing reaction kinetics, however, such use can result in a reduction in the amount of higher molecular weight hydrocarbons formed thereby.

It is also to be understood that in the hydrocarbon conversion methods of the invention, sources or forms of oxygen-containing gas other than air can be used or preferred. Thus, the oxygen-containing gas for use in the conversion methods of the invention can vary in molecular oxygen content from oxygen-depleted air, to air, to oxygen gas itself, for example. Air or enriched air can be a preferred source of molecular oxygen.

Such oxidative coupling processing of methane, when air is used as a source of oxygen, typically results in a gaseous mixture comprising ethane and ethylene, illustrative of saturated and unsaturated aliphatic hydrocarbon products having higher molecular weights than the feedstock alkanes from which they were formed, and possibly some traces of aromatics or higher hydrocarbons which may form in the reactor, such as at high operating temperatures, for example, at temperatures greater than 750° C., as well as carbon monoxide, carbon dioxide, nitrogen, water, any remaining unreacted feedstock alkane and oxygen. It being understood that conventional catalytic processing schemes, such as refining hydrotreatment, are typically conducted at operating temperatures of only about 400° C. to 450° C.

Such a reaction product mixture may illustratively be used as chemical feedstock or be further reacted, such as occurs during conversion, to form gasoline type hydrocarbon products. For example, the effluent with desired or required pretreatment, e.g., $H_2O$ removal, and/or downstream treatment, e.g., $N_2$ removal, may be passed over a suitable aromatization/oligomerization catalyst (such as a crystalline borosilicate or aluminosilicate molecular sieve material or supported phosphoric acid) to produce desired gasoline-type hydrocarbon products. Other specific uses of the reactor effluent will be apparent to those skilled in the art.

In the above-described embodiment, methane and oxygen (as a part of air) are simultaneously contacted with the oxidative coupling contact material. Such operation is commonly referred to as "cofeed" operation and in such operation, oxygen, which may be needed for the coupling reaction to occur, is also fed to the reactor rather than exclusively being carried into the reactor via the lattice of the contact material, as may be typical of "redox" operation, as described above. Further, cofeed operation may minimize or eliminate the need for subsequent reoxidation of the contact material such as may be required to resupply lattice oxygen to contact materials such as those which typically contain reducible metal oxides as typically is required when such contact materials are utilized in a redox mode operating scheme.

Generally, a suitable feedstock for the method of this invention comprises at least one of methane, ethane and propane and preferably comprises mostly methane, e.g., at least about 75 percent methane, and more preferably may be methane as methane is typically the predominant hydrocarbon reserve component which is desired to be converted to a higher molecular weight hydrocarbon. Thus, a suitable feedstock for the method of this invention comprises natural gas, gases formed during mining operations and petroleum processes or in the above- or below-ground gasification or liquefaction of coal, tar sands, oil shale and biomass, for example.

The contacting of the hydrocarbon feedstock with the oxygen-containing gas and in the presence of the contact material generally is performed at oxidative coupling reaction conditions including temperature and pressure. Preferably, such contacting is performed at a temperature in the range of from about 600° C. to about 1,000° C. and, more preferably, in the range of from about 700° C. to about 900° C. These temperature ranges have been found to be preferred as operation at temperatures below about 600° C. may generally result in the contact material having relatively unfavorable product (e.g., $C_{2+}$ hydrocarbons) selectivities while operation at higher temperatures, e.g., temperatures greater than about 900° C., can result in generally undesirable thermal reactions seriously competing with coupling reactions. The products resulting from such thermal reactions will typically be largely comprised of $H_2$, $CO_x$ (where $x=1$ or 2) and may also include coke, acetylene and aromatics such as benzene, for example. Such thermal reactions will typically overwhelm the desired coupling reactions when temperatures exceed about 1,000° C. It is to be understood, however, that at higher reaction temperatures at least trace quantities of aromatic compounds may also form.

The contacting of the hydrocarbon feedstock and oxygen with the contact material is preferably performed under a total absolute pressure in the range of from about 0.1 atmosphere to about 10 atmospheres, and more preferably in the range of from about 1 atmosphere to about 5 atmospheres, as operation at pressures exceeding this range typically results in reduced $C_{2+}$ product selectivities while subatmospheric operation is believed to be economically unattractive as capital expenditures escalate rapidly for a system to be capable of handling the actual volumes of gas required for such a commercial operation.

The ratio of the partial pressure of the combined feedstock alkanes containing from 1 to 3 carbon atoms to the oxygen partal pressure at the entrance of the reactor in the contacting step is preferably in the range of from about 2:1 to about 40:1 and, more preferably, in the range of from about 2:1 to about 10:1, as operation at lower $C_1$–$C_3$ alkane to oxygen partial pressure ratios generally results in excessive carbon oxide formation, while operation at higher ratios may result in insufficient amounts of oxygen being present to obtain desired levels of conversion and consequently results in the remainder of greater amounts of unreacted hydrocarbon reactant. The combined partial pressures of the alkanes in the feedstock containing from 1 to 3 carbon atoms at the entrance to the first reactor (the contacting reactor) is preferably no more than about 10 atmospheres, and, more preferably, no more than about 4 atmospheres. The oxygen partial pressure at the entrance to the first reactor is preferably no more than about 4 atmospheres and, more preferably, no more than about 2 atmospheres. The oxygen partial pressure in the gaseous effluent from the reactor in the contacting step is preferably substantially 0.

In view of the highly active nature of the subject contact materials for the oxidative conversion of lower alkanes to a product composition containing higher molecular weight hydrocarbons, the contacting step is preferably performed at a space velocity of from about 1,000 to about 1,000,000 volumes of total feed gas at ambient conditions per volume of catalytic composition per hour and more preferably at a space velocity of about 50,000 to about 200,000 volumes of total feed gas per volume of catalytic composition per hour, as thermal reactions will generally predominate with operation at lower space velocities while oxygen conversion will generally be unsuitably incomplete with operation at higher space velocities.

The high activity of the subject contact materials combined with the release of large amounts of heat associated with the exothermic oxidative coupling reaction of lower alkanes, makes heat transfer and temperature control significant engineering challenges to commercial operation of the process. Reactors particularly suited for use in the practice of the invention need to allow for heat transfer and permit desired temperature control. Such reactors can include certain types of fluidized bed reactors wherein the contact material is finely divided as this promotes a more rapid heat transfer as well as tubular reactors wherein the contact material is directly applied to the reactor wall to promote heat transfer and to permit desired temperature control.

The present invention provides an intimately mixed contact material composition substantially free of a catalytically effective reducible metal oxide and containing at least three different cationic species. In its broader aspects, the contact material composition of this invention comprises, consists of, or consists essentially of an intimately mixed, mixed oxide containing:

a) at least one cationic species of a naturally occurring Group IIIB element;

b) at least one cationic species of a Group IIA metal selected from the group consisting of magnesium, calcium, strontium and barium; and c) a cationic species of zirconium or hafnium.

It has been found that materials with an intimate mixture of at least one cationic species of a Group IIIB and at least one cation species of a Group IIA metal, selected from the group consisting of magnesium, calcium, strontium and barium, have improved performance characteristics, e.g., higher $C_{2+}$ selectivities when used in the oxidative coupling processing of methane, as compared to the corresponding contact materials wherein the Group IIIB species and the Group IIA species are used alone or in which the species are present in a non-intimately mixed fashion.

It has been further found that a cationic species of zirconium or hafnium in the intimate mixture results in a contact material with improved stability and improved physical properties such as improved hardness and attrition resistance, as is desired when fluidizable contact materials are sought, as compared to similar materials but which do not contain an intimately mixed zirconium or hafnium species.

Such compositions will preferably contain no more than about 75 weight percent zirconium or hafnium and, more preferably, will contain zirconium or hafnium in an amount in the range of about 10 to 55 weight percent of the contact material composition. (Such weight percents being on an elemental basis). Such relative amounts of zirconium and hafnium in the contact materials of the invention are preferred because they result in more active and selective contact materials, e.g., in the oxidative coupling of methane, such contact materials result in higher conversions and selectivities to $C_{2+}$ hydrocarbons. In addition, more than nominal amounts of zirconium and/or hafnium, i.e., typically more than about 1 to 2 weight percent on an elemental basis, is believed required. It is theorized that zirconium and hafnium act to keep the Group IIA metal, e.g., barium, from volatizing out of the contact material. For example, relatively stable Ba-Zr and Ba-Hf oxide phases, respectively, are formed, and serve to deter or avoid such volatization.

Also, in such compositions, the cationic species of the Group IIIB element and the Group IIA metal are preferably present in an approximate molar or atomic ratio of about one Group IIIB element cationic species to about 0.001 to about 100 Group IIA metal cationic species and, more preferably, in a ratio of about 1 Group IIIB element cationic species to about 0.5 to about 3 Group IIA metal cationic species, and even more preferred, a ratio of about 1 Group IIB element cationic species to about 1.5 to about 2.5 Group IIA metal cationic species.

In one preferred embodiment of the invention, the Group IIIB element is selected from the group consisting of yttrium, lanthanum, neodymium, samarium and ytterbium, as Group IIB elements which form oxides that do not have a +4 oxidation state. Our experience has been that accessibility to a higher oxidation state, e.g., an oxidation state of +4, leads to contact materials which have poorer selectivity and are more susceptible to reduction, e.g., are susceptible to reduction to a +3 oxidation state, i.e., are reducible metal oxides, and can thus lead to loss of physical strength or lead to increased carbon oxide formation.

In a particularly preferred embodiment the Group IIIB element cationic species is yttrium, at least in part because of the comparative general availability of yttrium.

In one preferred embodiment of the invention the Group IIA metal cationic species will be either strontium or barium, as contact materials containing strontium or barium, as opposed to similar compositions which instead contain other Group II metals or no Group IIA metals at all, generally exhibit a greater selectivity to higher hydrocarbons when the materials are used in oxidative coupling of lower alkanes. The greater selectivity of the subject compositions containing strontium or barium is believed, at least in part, to result from strontium and barium having a preferred ionic size and basicity, as compared to the other Group IIA metals. It is believed that the ionic size of strontium and barium, as being generally more similar to Group IIIB metals, facilitates their incorporation into the material. In addition, basicity is believed to contribute to the ability of the resulting contact material to perform such as in the ability of the contact material to abstract hydrogen from the methane molecule in the oxidative coupling of methane, for example.

One preferred composition of the invention comprises a mixed oxide of cationic species of a) yttrium, b) strontium or barium, and c) zirconium or hafnium, with such compositions containing zirconium and/or hafnium in an amount of no more than about 80 weight percent and, more preferably about 10 to 55 weight percent of the contact material composition and with the approximate molar or atomic ratios of strontium and/or barium to yttrium being in the range of about 0.001 to about 100 (that is about 0.001 to about 100 moles/atoms of strontium and/or barium per mole/atom of yttrium) and, more preferably, in a ratio in the range of about 0.5 to about 3 and, even more preferred, in the range of about 1.5 to about 2.5.

One compositional embodiment of the invention can be represented by the chemical formula:

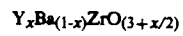

$$Y_xBa_{(1-x)}ZrO_{(3+x/2)}$$

where $0<x<1$. It has been found that as the value of x approaches 1, the material is not very active for the oxidative conversion of methane to $C_{2+}$ hydrocarbons. As the value of x approaches 1, a yttrium zirconium oxide is formed. In addition, as the value of x approaches 0, the predominant phase is believed to be barium zirconate perovskite. When the value of x is some intermediate between 0 and 1, preferably, when the value of x is in the range of about 0.3 to about 0.7 and, more preferably, when the value of x is about 0.5, the material comprises a mix of three phases, e.g., barium carbonate, barium zirconate and yttrium zirconate, and generally exhibits better rates of oxygen conversion and better selectivity to $C_{2+}$ products in the oxidative conversion of methane to higher hydrocarbons, as compared materials represented by such a chemical formula but having differing values of x.

Typically, the contact material compositions of the invention will have surface areas generally in the range of about 0.1 m²/gram to about 100 m²/gram and preferably have surface areas in the range of about 1 m²/gram to about 10 m²/gram as such compositions having surface areas in this range generally result in better performance in terms of selectivity and activity, e.g., better $C_{2+}$ selectivity and methane conversion in the oxidative conversion of methane to a higher molecular weight hydrocarbon, as compared to similar compositions with a surface area outside such ranges.

The subject compositions by being substantially free of catalytically effective reducible metals are not susceptible to over-reduction or over-oxidation and the difficulties associated with such changes, as are those compositions containing reducible metal oxides. In addition, the subject contact material compositions are sufficiently hard so that they can be used to form a material that can be fluidized without large losses of material in the form of fines.

The contact material compositions of the invention may be prepared by any suitable method associated with suitable compositions known in the art. Thus, sol-gel preparation techniques, as well as physical mixing techniques, for example, can be used to produce the composition.

The precursor materials resulting from these preparation techniques will typically be calcined at a temperature and for a duration sufficient to lead to a stabilizing interaction among the principal metal cations of the material, whereby solid state transformations typically occur and the material becomes more homogeneous, e.g., "intimately mixed." For example, the precursors can be calcined at 800° C. for 8 to 12 hours. In such preparations, the components can be characterized as being intermixed on a microscopic scale (e.g., about 100 micron particle size) and with the components interacting to stabilize and form compound(s) containing more than one of the cationic species. For example, a sol-gel preparation method using barium nitrate, yttria sol and zirconia sol when calcined to 800° C., produced a very homogenous sample. It is to be understood that such calcination generally results in a stabilizing interaction among the constituents of the material.

Generally, it is preferred to prepare the subject compositions using peroxide, oxide, carbonate and/or hydroxide precursors containing the selected cationic species, which precursors do not contain significant relative amounts of volatile organic species which upon decomposition can act to undesirably increase the surface area of the composition.

It is to be understood that exposure to high temperatures (e.g., about 700° C. to about 1,000° C. and such as occurs during calcination or, less preferably, in the process use of the material, such as in the oxidative conversion of lower molecular weight alkanes to higher molecular weight hydrocarbons) can and generally will result in desired stabilizing interaction among the constituents of the material. Further, an increase in the homogeneity of the material is observed with the use of the material under oxidative coupling reaction conditions.

Alternatively, such compositions can be prepared via physical mixtures of appropriate metal oxides and/or salts. As will be shown in the examples below, appropriate metal oxides/salts such as yttrium carbonate, barium hydroxide and zirconium oxide can be used. Other appropriate metal oxides/salts include nitrates such as barium nitrate, yttrium nitrate and zirconium dinitrate oxide, carbonates such as barium carbonate, acetates such as barium acetate, as well as materials such as yttrium oxide, for example.

The contact materials of the invention can also be used in oxidative conversion processes to produce dehydrogenated and/or lighter products.

One such application for the compositions of the invention is the oxidative dehydrogenation of dehydrogenatable hydrocarbons and compounds, specifically processing in which the carbon framework of the hydrocarbon feedstock is substantially retained but with the removal of hydrogen therefrom. The process comprises contacting a gas or liquid comprising a dehydrogenatable hydrocarbon or compound with oxygen in the presence of the subject contact material to produce dehydrogenated hydrocarbons and coproduct water. Carbon oxides, i.e., CO and $CO_2$, and hydrogen can also be formed as by-products of the overall reaction, it being understood that hydrogen by-product can also be formed as a result of watergas shift reaction.

Dehydrogenatable hydrocarbons include a wide variety of hydrocarbons including $C_{2+}$ alkanes, cycloalkanes, olefins, alkylaromatics, etc., for example. As used herein, dehydrogenatable hydrocarbons are understood to also include various forms of oxygen-containing hydrocarbons such as alcohols (e.g., methanol, ethanol, propanol and butanols) and aldehydes (e.g., ethanol, propanol and butanol) and mixtures thereof with and without other dehydrogenatable hydrocarbons.

The dehydrogenated product depends in part on the feedstock selected. For example, alkanes can be dehydrogenated to form olefins, diolefins, alkynes, etc., olefins can be dehydrogenated to form diolefins, alkynes, etc., aldehydes can be dehydrogenated to form unsaturated aldehydes and alcohols can be dehydrogenated to form aldehydes, for example. One preferred class of feedstock comprises $C_2$-$C_6$ alkanes. One preferred process embodiment comprises oxidative dehydrogenation of $C_2$-$C_6$ alkanes to form corresponding mono-olefins.

Conditions for oxidative dehydrogenation processing include an operational temperature generally lower than the temperatures preferred for oxidative coupling processing. For example, the temperature for oxidative dehydrogenation processing is generally preferably in the range of about 300° C. to about 650° C. whereas temperatures for the oxidative coupling of methane are typically preferably greater than 700° C. Operating pressures are not narrowly critical and can range from subatmospheric to pressurized operation. In addition, and at least in part, as a result of operation at lower operating temperatures, operating pressures for oxidative dehydrogenation can be greater than the pressures preferred for the oxidative coupling of lower alkanes such as methane, for example. Lower operating temperatures typically can result in decreased gas phase reaction contributions. Gas phase reactions often are free radical in nature. The collision of radical species with oxygen in the gas phase, however, often leads to the undesirable formation of carbon oxides. While increasing the pressure increases the frequency of gas phase collisions, to the extent that gas phase reaction contributions are decreased as a result of lower operating temperatures usable in oxidative dehydrogenation, the pressure can be increased without a deleterious increase in carbon oxides formation. Generally, for economic reasons, operational pressures of a few hundred pounds per square inch will be preferred for oxidative dehydrogenation processing, as pressures in this range are generally more conducive to economical separation processing and for the optimization of compressor operation and cost.

In oxidative dehydrogenation processing, the ratio of the partial pressure of the dehydrogenatable hydrocarbon feedstock to the partial pressure of the feed oxygen is preferably in the range of from about 0.5:1 to about 40:1 and, more preferably, in the range of from about 1:1 to about 20:1.

The lower limit of the ratio of hydrocarbon feedstock to feed oxygen is generally limited by the flammability range for the feed blend. While some fluid bed reactors can operate with flammable feed blends, such operation is generally undesirable due to safety concerns. In turn, as low conversions per pass typically results in either the unproductive use of feed or to the typically costly recycle of unreacted feed, the upper limit of hydrocarbon to oxygen ratio is generally limited by the need to attain acceptable per pass conversion rates of feed.

As compared to conventional dehydrogenation processing, oxidative dehydrogenation processing advantageously can result in higher conversions, operate at higher pressures without thermodynamic considerations limiting the conversion per pass, generally proceeds through exothermic reactions and is not limited by coke formation as is typically found in conventional dehydrogenation processing. In addition, the exothermic nature of the reactions involved in oxidative dehydrogenation processing can provide at least a significant portion of the heat necessary to bring the reactants up to the desired operating temperature and keep the reactants at the operating temperature during reaction, thus simplifying the heat transfer equipment needed in the operation of the process.

Conventional dehydrogenation is limited by thermodynamic considerations and typically results in the production of hydrogen and a dehydrogenated product. The amount of hydrogen present limits the equilibrium conversion to dehydrogenated product since hydrogen and the dehydrogenated product can react, e.g., rehydrogenate the dehydrogenated product. As conventional dehydrogenation reactions are generally endothermic in nature, increasing the system operating temperature can serve to reduce the effect of such an equilibrium limitation. As the endothermic reactions occur, the temperature in the system decreases until an equilibrium limitation is reached. Significant process system complications result when the operating system is required to provide the amounts of heat required to counter equilibrium limitations and the endothermic nature of the conventional dehydrogenation reaction. In addition, as the system operating temperature is increased, the amount of extent of carbon or coke formation in such processing can become more significant. Consequently, most commercial conventional dehydrogenation processes involve coke removal steps which are typically relatively costly.

While the oxidative dehydrogenation processing of the invention does not result in significant coke formation, the processing does produce at least some carbon oxides. Generally, conventional dehydrogenation processing does not produce such carbon oxides. In the manufacture and production of transportation fuels or fuel additives, the carbon oxides and hydrogen coproduced with the dehydrogenated products can be used or further processed, such as through Fischer-Tropsch processing, such as is applicable to the processing of synthesis gas (also commonly referred to as "syngas"), e.g., a mixture of $H_2$ and CO, with or without the presence of $CO_2$. Furthermore, for continuous operation of non-chemical grade olefin production, such as in the manufacture of fuel components, carbon oxide formation is much preferred over coke formation and the problems attendant coke removal processing.

Another specific application for the compositions of this invention is the oxidative cracking of crackable hydrocarbons and compounds. The process comprises contacting a gas or liquid comprising a crackable hydrocarbon or compound with oxygen in the presence of the subject contact material to produce cracked hydrocarbons/compounds. In addition, water and carbon oxides (i.e., carbon monoxide and/or carbon dioxide) as well as some hydrogen, will also typically be produced.

Crackable hydrocarbons include a wide variety of hydrocarbons including $C_{3+}$ alkanes, cycloalkanes, alkyl aromatics, etc., for example.

The cracked product depends, in part, on the feedstock selected. Usually, the cracked product will contain olefinic hydrocarbons, e.g., molecules having carbon-carbon double bonds. One preferred class of feedstock comprises $C_3$–$C_6$ alkanes. One preferred process embodiment comprises oxidative cracking of $C_3$–$C_6$ alkanes to form a cracked product including ethane, ethene, propane, propene, butane and butenes, for example.

Oxidative cracking processing differs significantly from conventional steam cracking processing. Primary areas of difference include heat balances, the formation of carbon oxides and desired unit operation conditions. For example, oxidative cracking processing is an exothermic process which can provide heat needed to raise the temperature of the reactants to the desired cracking operating temperature and to keep the reactants at a desired temperature range during processing, thus simplifying the heat transfer equipment needed for such processing. Generally, oxidative cracking processing has an operational temperature towards the higher end of the operational temperature range for oxidative dehydrogenation processing but less than that of oxidative coupling processing. For example, the operational temperature for oxidative cracking processing is generally preferably in the range of about 450° C. to about 650° C. with an operational temperature in the range of about 500° C. to about 550° C. being generally more preferred.

In addition, oxidative cracking is an exothermic process. The heat so generated can be used to heat the reactants to the desired operating temperature and keep the reactants at the operating temperature during reaction, thus simplifying the heat transfer equipment needed in the operation of the process. Generally, the hydrocarbon to oxygen ratios for use in oxidative cracking processing are in the same general range as those previously identified for used in oxidative dehydrogenation processing and are typically limited by the same factors of flammability limits and the economic need for an adequate per pass conversion rate.

In addition, other forms or modes of hydrocarbon cracking typically result in the formation of coke. Generally, such coke can act to foul heat exchange surfaces, e.g., in conventional tubular cracking reactors, coke fouling the heat exchange surfaces generally will serve to decrease the rate of heat transfer. Also, as detailed above, carbon/coke formation and the removal of such carbon/coke typically results in a loss in process productivity. In contrast, in oxidative cracking processing, carbon oxides are formed as opposed to carbon/coke formation. The carbon oxides so formed can be processed as addressed above in the description of oxidative dehydrogenation.

Since the oxidatively driven reactions are not as limited by equilibrium considerations, oxidative cracking processing can be operated at higher pressures than conventional cracking reactions. Higher pressures, such as operating pressures of a few hundred pounds per square inch, are desirable as such high pressures can result in increased efficiency in operating downstream separation processes and in matching desirable operating pressures for downstream conversion processes. Preferred operating pressure ranges generally range from about 0.5 atmospheres absolute to about 100 atmospheres absolute, with operating pressures in the range of about 2 to about 50 atmospheres absolute generally being more preferred. It is understood that the operation of gas reaction processes at elevated pressures results in reducing the size of processing vessels required and thus generally reduces the cost of the vessels and of the associated equipment for compression of products. In cracking processing, the volumes of cracked products as gases are greater than the volumes of the reactants as gases. In such processing, it is generally less expensive to compress the reactants and operate the reactor under pressure rather than compress the gases from a lower pressure reactor.

As will be appreciated from the above discussion of dehydrogenated products resulting from the oxidative dehydrogenation of a dehydrogenatable hydrocarbon and cracked products resulting from the oxidative cracking of a crackable hydrocarbon, such dehydrogenated products can and frequently do contain at least some cracked hydrocarbons and such cracked products can and frequently do contain at least some dehydrogenated hydrocarbons.

It is also to be understood that the contact material of the invention can also have applicability in non-oxidative dehydrogenation and non-oxidative cracking, that is in dehydrogenation and cracking in the substantial absence of oxygen. Such non-oxidative processing is generally under similar reaction conditions as those generally stated above for corresponding oxidative conversion processing.

The contact materials and the processes utilizing the subject contact materials illustratively disclosed herein can suitably be practiced in the absence of any component or ingredient or process step, respectively, which is not specifically disclosed herein.

The present invention is described in further detail in connection with the following examples which illustrate various aspects involved in the practice of the invention. It is to be understood that all changes that come within the spirit of the invention are desired to be protected and thus the invention is not to be construed as limited by these examples.

EXAMPLES

Example 1

Preparation by physical mixture of a contact material having the nominal composition $YBa_2Zr_3O_x$, where $x$=a molar amount necessary for the contact material composition to be at stoichiometric balance, for the nominal composition, $x=9.5$.

Yttrium carbonate, $Y_2(CO_3)_3 \cdot 3H_2O$ (6.18 gm, 0.015 mole), was physically mixed using a mortar and pestle with barium hydroxide, $Ba(OH)_2 \cdot 8H_2O$ (19.12 gm, 0.0606 moles), and zirconium oxide, $ZrO_2$ (11.10 gm, 0.0909 mole). The waters of hydration were enough to make the precursors turn into a sticky paste when ground together. This material was placed in MgO clay crucibles and calcined in air as follows: The sample was placed in a programmable electric furnace and heated to 400° C. by increasing the temperature at the rate of 2° C./min, then maintained at 400° C. for 1 hour, followed by heating to 800° C. by increasing the temperature at the rate of 2° C./min, then maintained at 800° C. for 5 hours, and then finally cooled. A tan colored powder was recovered that was determined by XRD to have the following crystalline phases: $BaCO_3$ 5-378, and $ZrO_2$ 36-420, 24-1164 as well as poorly crystalline barium zirconate. (The numbers refer to the X-ray file numbers given to known materials cataloged in the Powder Diffraction File). The yttrium phases remained amorphous. Surface area was determined to be 2.6 $m^2/gm$ by Kr digisorb analysis. The average pore radius was 4,038 Å with a bulk density of 1.01 gm/ml as determined by Hg porosimetry.

The contact material was sieved to 80/100 mesh and diluted 10:1 with 30/50 alpha alumina.

Example 2

Preparation of a sol-gel mixture, contact material having the nominal composition $YBa_2Zr_3O_x$, where $x$=a molar amount necessary for the contact material composition to be at stoichiometric balance, for the nominal composition, $x=9.5$.

Barium carbonate, (31.638 gm, 0.1603 mole) was weighed into a 1 liter beaker along with 200 ml of distilled water. This slurry was heated to 75° C. and concentrated nitric acid was added dropwise until no more $CO_2$ was given off and all the solid $BaCO_3$ dissolved into solution as $Ba(NO_3)_2$. The resulting pH was near 1 at 50° C. To this solution was added 64.65 gm of cloudy yttria sol (Nyacol, 14% solids) which was added dropwise. This caused the solution to become more cloudy and viscous and brought the pH up to 6-7. Finally a clear $ZrO_2$ sol (148.16 gm, Nyacol, 20% solids) was added causing the solution to become more clear yet more viscous. The pH remained at 7 at 50° C. and after a minute the sol turned into a thick clear gel while cooling to room temperature. After placing the gel in a hood to dry overnight, it was further dried in a vacuum oven with air purge for 2 days at 85°–100° C. and at 25 inches of water pressure. A homogeneous crystalline white powder was formed which was placed in a quartz crucible and calcined in air as follows: The sample was placed in a programmable electric furnace and heated at 5° C./min to 400° C., held at that temperature for 1 hour, heated at 2° C./min to 800° C., held at that temperature for 5 hours, then cooled. By XRD the material was highly crystalline and predominantly a new Ba-(Y)$ZrO_3$ perovskite where $Y_2O_3$ is in solid solution with $BaZrO_3$. The cubic unit cell has a dimension of 4.21801 Å, 36 standard deviation larger than the known $BaZrO_3$ whose cell dimension is 4.18150 Å. This phase remains after the catalyst has been used. A minor phase of $BaCO_3$ was also present. Again no crystalline $Y_2O_3$ was observed. The bulk density was 1.8 gm/ml and the surface area was only 0.27 $m^2/gm$.

Example 3

Quantification of the amount of yttria incorporated into the Ba(Y)$ZrO_3$ perovskite of the contact material of Example 2.

The contact material of Example 2 was analyzed by scanning transmission electron microscopy-energy dispersive X-ray (STEM-EDX). The sample was first ground to a fine powder. The powder material was mixed with an epoxy resin embedding material and then allowed to harden. After hardening, the material was placed in a microtome wherein a diamond knife was used to slice very thin sections from the embedded material. Two phases (phases "B" and "C") of Ba(Y)ZrO$_3$ were observed. Phase "B" comprised polygonal crystallite clusters and contained approximately 2.4 atomic % Y in BaZrO$_3$. Phase "C" comprised fine particle clusters and contained 6 to 10 atomic % Y in BaZrO$_3$. The only other phase detected by STEM-EDX, (phase "A"), comprised dense solid particles, did not contain Ba and had a composition of 6.5 atomic % Y and 27.4 atomic % Zr with the balance being oxygen.

See Table 1 for the STEM-EDX results.

TABLE 1

| | Sample area | STEM-EDX (atom %) | | | |
|---|---|---|---|---|---|
| | | Y (as Y$_2$O$_3$) | Ba (as BaO) | Zr (as ZrO$_2$) | O (by diff) |
| Phase "A" | 1 | 6.5 | 1.3 | 27.1 | 65.2 |
| | 2 | 6.6 | 0.4 | 27.6 | 65.4 |
| Phase "B" | 3 | 2.4 | 18.3 | 19.1 | 60.2 |
| | 4 | 2.5 | 18.0 | 19.2 | 60.2 |
| | 5 | 2.2 | 18.0 | 19.4 | 60.3 |
| | 6 | 2.4 | 18.4 | 19.1 | 60.1 |
| | 7 | 4.0 | 16.6 | 18.9 | 60.5 |
| | 8 | 2.4 | 18.2 | 19.2 | 60.2 |
| | 9 | 2.4 | 17.9 | 19.4 | 60.3 |
| Phase "C" | 10 | 10.2 | 15.4 | 14.6 | 59.8 |
| | 11 | 5.9 | 20.4 | 14.8 | 58.9 |
| BaZrO$_3$ reference sample | 12 | 0.1 | 18.8 | 20.7 | 60.4 |
| | 13 | 0.5 | 18.4 | 20.7 | 60.5 |
| | 14 | 0.2 | 18.8 | 20.6 | 60.4 |
| | 15 | 0.0 | 18.5 | 21.0 | 60.5 |
| | 16 | 0.0 | 18.5 | 20.4 | 60.2 |
| | 17 | 0.0 | 14.1 | 23.9 | 62.0 |
| | 18 | 0.0 | 19.3 | 20.4 | 60.2 |
| stoichiometric values | | | 20.0 | 20.0 | 60.0 |

Example 5

The contact material of Example 1 was tested for oxidative conversion of methane to higher hydrocarbons.

The contact material was sieved to 80–100 mesh, diluted 10:1 with inert 30–50 mesh alpha alumina diluent and loaded in a plug flow reactor containing a three zone electric tube furnace that heats a 14 mm I.D., 16 mm O.D. quartz tube with a 4 mm O.D. thermowell. Feedstock gas blends were 47% CH$_4$, 4.7% O$_2$ with the balance being N$_2$. Nitrogen was used as an internal standard for the gas analysis which was done with an on-line gas chromatograph. Mass balances of 100 +/−1% were obtained. Relative feed rates of 72,000 standard cc per hour per cc contact material were used unless otherwise stated.

See Table 2 for reaction conditions and product selectivities.

TABLE 2

| REACTION CONDITIONS | | | |
|---|---|---|---|
| Temperature °C. (Avg.) | 697.0 | 748.0 | 801.0 |
| SV (1/hr) | 72375 | 72375 | 72375 |
| CH$_4$/O$_2$ mole ratio | 10.491 | 10.491 | 10.491 |
| O$_2$/CH$_4$ mole ratio | .095 | .095 | .095 |
| O$_2$ conv., mole % | 28.49 | 51.82 | 85.68 |
| CH$_4$ conv., mole % (1) | 3.51 | 7.98 | 14.44 |
| CH$_4$ conv., mole % (2) | 3.72 | 8.29 | 14.44 |
| Res. time (sec) | .005 | .005 | .005 |
| SELECTIVITIES, mole % | | | |
| CO | 19.67 | 9.50 | 5.03 |
| CO$_2$ | 27.42 | 20.05 | 16.27 |
| C$_2$H$_4$ | 5.88 | 16.33 | 30.19 |
| C$_2$H$_6$ | 45.68 | 50.32 | 42.97 |
| C$_2$H$_2$ | .00 | .00 | .11 |
| C$_3$'s | 1.35 | 3.80 | 5.16 |
| C$_4$'s | — | — | 0.26 |
| Sel. to C$_{2+}$ | 52.91 | 70.45 | 78.70 |
| C$_2$H$_4$/C$_2$H$_6$ | .13 | .32 | .70 |
| H$_2$/CO | 2.66 | 3.17 | 4.21 |
| CO/CO$_2$ | .72 | .47 | .31 |

(1) CH$_4$ conversion calculated from CH$_4$ in minus CH$_4$ out.
(2) CH$_4$ conversion calculated from carbon in products.

Example 6

The contact material of Example 2 was sieved to 80–100 mesh, diluted with inert 30–50 mesh alpha alumina diluent in a ratio of 20:1, rather than at a 10:1 ratio as used in Example 5, because of the higher density of the material of Example 2 and tested in the same manner as described in Example 5.

See Table 3 for reaction conditions and product selectivities.

TABLE 3

| REACTION CONDITIONS | | | | | |
|---|---|---|---|---|---|
| Temperature °C. (Avg.) | 701.0 | 754.0 | 794.0 | 836.0 | 862.0 |
| SV (1/hr) | 73491 | 73491 | 73491 | 73491 | 73491 |
| CH$_4$/O$_2$ mole ratio | 11.124 | 11.124 | 11.124 | 11.124 | 11.124 |
| O$_2$/CH$_4$ mole ratio | .090 | .090 | .090 | .090 | .090 |
| O$_2$ conv., mole % | 21.35 | 41.00 | 69.21 | 92.63 | 98.13 |
| CH$_4$ conv., mole % (1) | 2.93 | 6.57 | 11.39 | 14.58 | 15.15 |
| CH$_4$ conv., mole % (2) | 2.73 | 6.52 | 11.18 | 14.70 | 15.27 |
| Res. time (sec) | .005 | .005 | .005 | .005 | .005 |
| SELECTIVITIES, mole % | | | | | |
| CO | 23.77 | 12.57 | 8.67 | 7.10 | 5.38 |
| CO$_2$ | 22.49 | 17.05 | 15.81 | 16.13 | 17.31 |
| C$_2$H$_4$ | 5.94 | 17.38 | 30.51 | 39.10 | 42.97 |
| C$_2$H$_6$ | 46.55 | 49.63 | 40.87 | 31.99 | 28.44 |
| C$_2$H$_2$ | — | — | 0.14 | 0.34 | 0.64 |
| C$_3$'s | 1.24 | 3.36 | 4.00 | 4.75 | 4.37 |
| C$_4$'s | — | — | — | 0.59 | 0.87 |
| Sel. to C$_{2+}$ | 53.73 | 70.37 | 75.51 | 76.77 | 77.31 |
| C$_2$H$_4$/C$_2$H$_6$ | .13 | .35 | .75 | 1.22 | 1.51 |
| H$_2$/CO | .00 | .00 | .00 | .00 | .00 |
| CO/CO$_2$ | 1.06 | .74 | .55 | .44 | .31 |

(1) CH$_4$ conversion calculated from CH$_4$ in minus CH$_4$ out.
(2) CH$_4$ conversion calculated from carbon in products.

Results

FIG. 1 shows the conversion of oxygen varies with respect to reaction temperature and FIG. 2 shows the effect on C$_{2+}$ selectivity with varying reaction temperature realized with the use of the contact material of Example 1 (i.e., physical mixture) in Example 5 and with the use of the contact material of Example 2 (i.e., sol preparation) in Example 6.

Selectivities to carbon products and CH$_4$ conversions were calculated in the following manner:

(a) carbon selectivities were defined as the number of moles of carbon in a desired/specified product component relative to the total number of moles of carbon in all detected products and calculated accordingly.

(b) CH$_4$ conversion was determined by differences between the amount of CH$_4$ in the outlet and inlet (molar rates) and also by carbon balance, by the number of moles of product formed (assuming no carbon accumulation).

Deviations of the carbon mass balance from 100% was indicated by a difference in the two measures of CH$_4$ conversion. Since the reaction is oxygen limited and oxygen is a relatively expensive reactant to produce and process (e.g., separating oxygen from other gaseous species is generally relatively costly), the efficient utilization of oxygen is generally desired. Therefore, oxygen is usually completely consumed under optimal reaction conditions. Oxygen conversion climbed to 86% at 800° C. for the physical mixture and 98% at 862° C. for the sol-gel mixture. The slight decrease in activity of the sol preparation could be due to the lower surface area and higher bulk density compared to the physically mixed contact material. Selectivities to C$_{2+}$ hydrocarbons are similar for the contact materials of Examples 1 and 2 approaching 79-80% at 800° to 860° C. The only other major products were CO$_2$ and small amounts of CO.

Examples 7-12

Activity maintenance, and effect of total oxygen conversion and nitrogen dilution.

Examples 7 and 8

In Examples 7 and 8 the contact materials of Examples 1 and 2 in 0.05 gram samples, respectively, were each tested at 850° C. for oxidative conversion of methane to higher hydrocarbons for periods of time on stream of over 250 hours and 450 hours, respectively, at close to total oxygen conversion (e.g., a feed gas flow rate of 25 standard cubic centimeters per minute (sccm)) in order to determine if the contact materials degrade under such conditions. In this testing, a feed gas blend of 40% methane, 4% oxygen, and balance of nitrogen was passed over the contact material at the specified feed rate. Oxygen conversion and C$_{2+}$ selectivities (both in percents) versus total time on stream for the testing of the contact materials of Examples 2 and 1 are shown in FIGS. 3 and 4, respectively.

Figure 4:
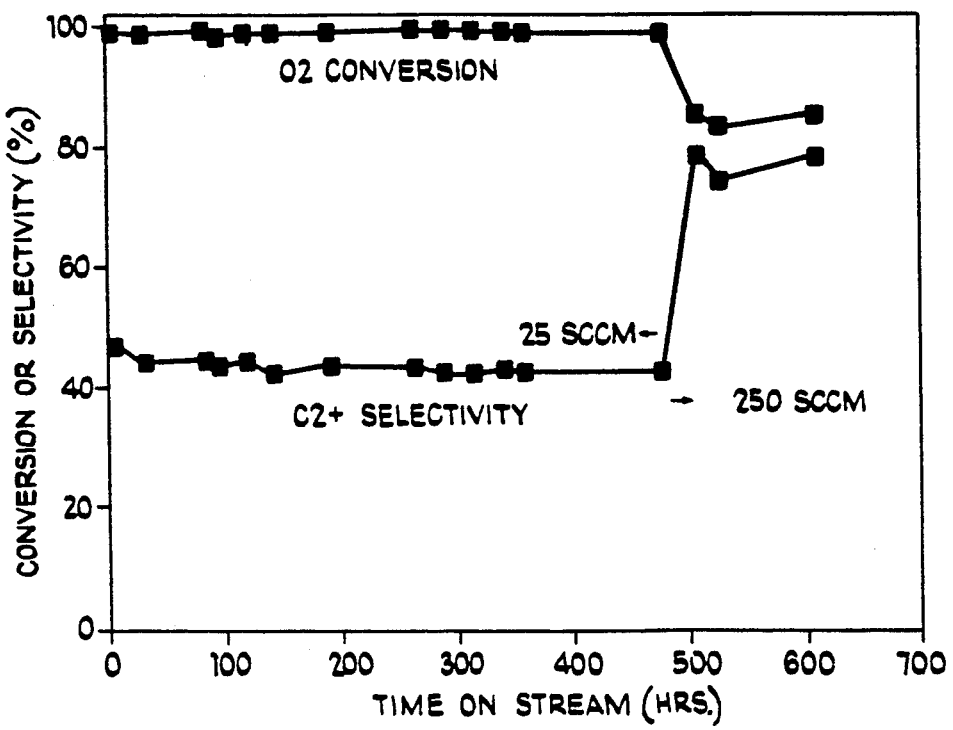

As can be seen in FIGS. 3 and 4, no deactivation was observed for either the contact material of Example 1 or 2 during this time period. This is in contrast to similar contact materials, but which materials contain reducible metals, e.g., tin, which convert into a combustion catalyst under similar conditions.

Example 9

After a time on stream of over 450 hours, the testing of the contact material of Example 1 for the oxidative conversion of methane to higher hydrocarbons of Example 8, was continued for a period of time of over 100 hours using the same feed gas blend as in Examples 7 and 8 but at a feed rate of 250 sccm.

The results (oxygen conversion and C$_{2+}$ selectivities in percents versus time on stream) are shown in FIG. 4.

Example 10

The contact material of Example 2 was tested in the manner of Examples 7 and 8, but with the specified feed gas blend passed over the contact material at the same 250 sccm feed rate as used in Example 9 with the contact material of Example 1.

Figure 5:
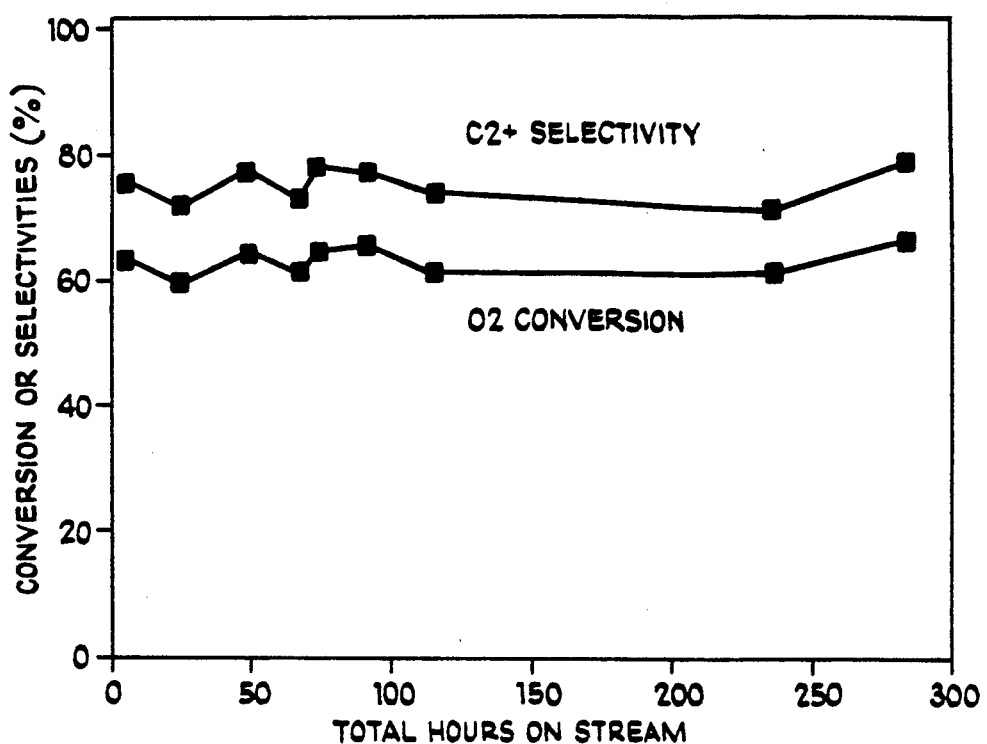

The results (oxygen conversion and C$_{2+}$ selectivities in percents versus time on stream) are shown in FIG. 5.

Additional Discussion of Results of Examples 7-10

FIG. 4 shows how an abrupt increase in feed flow rate causes a sharp increase in C$_{2+}$ selectivity and a corresponding decrease in oxygen conversion.

As shown in FIGS. 4 and 5, increasing the feed flow rate while increasing the C$_{2+}$ selectivity and reducing the oxygen conversion for the contact materials of Examples 1 and 2 did not cause a loss in activity maintenance.

The dependence of C$_{2+}$ selectivity on flow rate at high temperature is another unique feature of these tested contact materials.

The sol-gel preparation of Example 2 was less active in terms of oxygen conversion per standard weight of catalyst than the physically mixed contact material of Example 1. This may correlate with the higher bulk density of sol-gel preparation and its surface area being an order of magnitude lower than the contact material resulting from the physical mixture process of Example 1.

Examples 11 and 12

In order to understand how nitrogen dilution affects performance, runs were made in the manner of Examples 7 and 8 but with feed gases with and without nitrogen dilution and at varying feed flow rates. In the case of no nitrogen dilution, the feed gas contained pure methane and oxygen in a 10:1 CH$_4$:O$_2$ feed ratio. When nitrogen dilution was used, the feed gas still contained methane and oxygen in a 10:1 CH$_4$:O$_2$ ratio with the feed gas containing 40% CH$_4$, 4% O$_2$ and 56% N$_2$.

Discussion of Results

Figure 6:
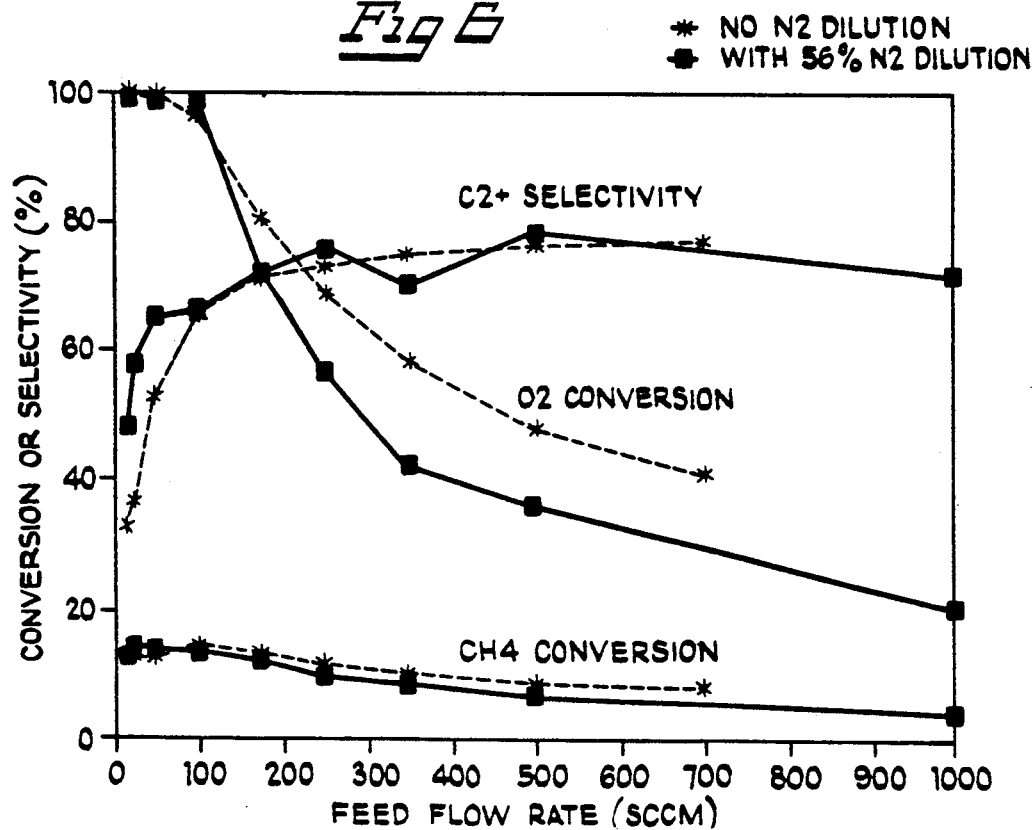
FIG. 6 is a graphical depiction of $CH_4$ conversion, $O_2$ conversion and $C_{2+}$ selectivity versus feed flow rate both with and without $N_2$ dilution for conversion of methane to higher molecular weight hydrocarbons according to typical embodiments of the invention.

FIG. 6 shows how the variation of feed flow rate affects various parameters with and without N$_2$ dilution. Very little change was observed in the C$_{2+}$ selectivity and the CH$_4$ conversion although oxygen conversion did increase with no N$_2$ dilution. No problems with coking or loss of temperature control were observed when using pure methane and oxygen in a 10:1 CH$_4$:O$_2$ feed ratio. FIG. 6 also suggests an optimum flow rate around 200 sccm at 850° C. to work at in order to maximize C$_{2+}$ yield.

In order to further test the robustness of the contact material, the contact material was run with pure CH$_4$ and oxygen for several hours at 850° C. after which the oxygen was shut off. Pure CH$_4$ flowed over the contact material for 5 hours before switching back to the original CH$_4$:O$_2$ mixture and the original conversion and selectivity came right back. Before the oxygen was shut off the C$_{2+}$ selectivity was 77%, CH$_4$ conversion was 8.6% and O$_2$ conversion was 48%. After the 5 hour treatment with pure CH$_4$ at 50 and 450 sccm the C$_{2+}$ selectivity was 75%, the CH$_4$ conversion was 8.9% and the O$_2$ conversion was 50%. This "shock" of exposure to a reducing atmosphere did not affect the performance of the contact material.

Example 13

To determine the effect of surface area and pore size distribution, several different preparations were made that resulted in materials having differing surface areas and pore sizes. Table 4 summarizes the different pore sizes and surface areas and the resulting performance for the different preparations in the oxidative conversion of methane to higher hydrocarbons. A feedstock gas blend having a mole ratio of methane to oxygen of 5 to 1 was used. In addition, a relative feed rate of 75 to 300 standard cubic centimeters per minute and a reactor temperature of 825° C.-850° C. were used.

TABLE 4

| Ave Pore Radius Å | Surface Area m²/gm | Total Int. Pore Vol. cc/gm | O₂ Conv. (%) | CH₄ Conv. (%) | C₂+ Sel. (%) | SV 1/hr | Temperature °C. |
|---|---|---|---|---|---|---|---|
| 297 | 17 | .41 | 95.6 | 19 | 40 | 8 × 10⁴ | 825 |
| 695 | 0.9 | .21 | 99.9 | 23 | 63 | 5.6 × 10⁴ | 825 |
| 989 | 1.1 | .32 | 97.1 | 23 | 60 | 4.7 × 10⁴ | 825 |
| 1031 | 1.3 | .55 | 97.4 | 23 | 60 | 5 × 10⁴ | 825 |
| 4038 | 2.6 | .75 | 98.2 | 24 | 64.5 | 4 × 10⁴ | 825 |
| 39747 | 0.3 | .27 | 99.2 | 24.5 | 65.3 | 9 × 10³ | 850 |

Descriptions of the different preparations

Preparation A—Average Pore Size=297 Å, Surface Area=17 m²/gm.

Zirconium oxynitrate, $ZrO(NO_3)_2 \cdot xH_2O$ (22.3 gm, $7.185 \times 10^2$ moles), was added along with yttrium nitrate, $Y(NO_3)_3 \cdot 6H_2O$ (3.1 gm, $8.094 \times 10^3$ moles) and barium nitrate, $Ba(NO_3)_2$ (4.236 gm, $1.621 \times 10^2$ moles) to a 500 ml beaker. This mixture of solids was dissolved in distilled water (200 ml) with gentle heating and stirring. An ethylene glycol/citric acid solution was prepared in a separate 250 ml beaker by dissolving 42.1 gm, 0.204 moles of citric acid into 150 ml of ethylene glycol. The citric acid solution was then added slowly to the metal salt solution while stirring. The mixture was then heated to 120° C. to drive off $NO_2$ and complex the metal salt with the citrate anion. After about 16 hours of heating at 120° C., the solution evaporated down to 90 ml and turned darker brown with some white precipitate falling out of solution. The material was vacuum dried for 3 days at 110° C. after which it turned to a tan colored solid. This solid was calcined in air using a quartz crucible as follows: The material was heated from 25° C. at 5° C./min to 400° C., held at that temperature for 1 hour and then heated at 2° C./min to 800° C. It was held at 800° C. for 8 hours before cooling back to 25° C.

Preparation B—Average Pore Size=695 Å, Surface Area=0.9 m²/gm.

Zirconium oxide, $ZrO_2$ powder (26.14 gm, 0.212 moles) was weighed in air into a mortar and pestle along with yttrium carbonate, $Y_2(CO_3)_3 \cdot 3H_2O$ (14.43 gm, 0.035 moles) and barium hydroxide, $Ba(OH)_2 \cdot 8H_2O$ (44.61 gm, 0.1414 moles). Upon grinding the powders together, a sticky paste was formed due to the waters of hydration in several of the precursors. The paste was then placed in a clay crucible and calcined in air as follows: The material was heated from 25° C. at 5° C./min to 400° C., held at that temperature for 1 hour and then heated again at 2° C./min to 800° C. The sample was held at 800° C. for about 5 hours before cooling to 25° C.

A portion of the calcined material was pelletized by placing 4.6 gm of powder in a 1 ⅛ inch die and applying 20,000 psig pressure to it. The pellet was recalcined in air by heating at 3° C./min from 25° C. to 800° C. and holding at that temperature for 5 hours before cooling to about 25° C.

Preparation C—Average Pore Size=989 Å, Surface Area=1.1 m²/gm.

A portion of the calcined material prepared in Preparation B (4.6 gm) was physically mixed with 1.0 gm of Sterotex binder, an organic, animal fat based material. The mixture was pelletized using a 1 ⅛ inch die and compressing to 20,000 psig. The pellet was calcined in air by heating at 3° C./min from 25° C. to 800° C. and holding at that temperature for 5 hours before cooling to about 25° C.

Preparation D—Average Pore Size=1031Å, Surface Area=1.3 m²/gm.

A portion of the calcined material prepared in Preparation B (4.6 gm) was mixed with 2.0 gm of Sterotex powder and pelletized. Pelletizing was done using a 1 1/8 inch die and compressing the powder to 20,000 psig. The pellet was then calcined in air by heating at 3° C./min from 25° C. to 800° C. and holding at that temperature for 5 hours before cooling to 25° C. again.

Preparation E—Average Pore Size=4038 Å, Surface Area=2.6 m²/gm.

A physical mixture was made by grinding together dry powders of zirconia, $ZrO_2$ (11.2 gm, 0.1815 moles); barium hydroxide, $Ba(OH)_2 \cdot 8H_2O$ (19.12 gm, 0.06061 moles) and yttrium carbonate, $Y_2(CO_3)_3 \cdot 3H_2O$ (6.18 gm, 0.015 moles) in a mortar and pestle. The powder turned into a sticky paste upon grinding due to waters of hydration. This paste was transferred to a clay crucible for calcination in air. Calcination was as follows: The sample was heated from 25° C. at a rate of 2° C./min to 400° C., held at that temperature for 1 hour and then heated at the rate of 2° C./min to 800° C. It was held at 800° C. for 5 hours before cooling to 25° C.

Preparation F—Average Pore Size=39747 Å, Surface Area=0.3 m²/gm.

Distilled water (200 ml) was heated to 85° C. in a 500 ml beaker. Barium nitrate, $Ba(NO_3)_2$ (10.000 gm, 0.03824 moles ) was dissolved into the water with stirring followed by yttrium nitrate, $Y(NO_3)_3 \cdot 6H_2O$ (5.26 gm, 0.01914 moles) and zirconium oxynitrate, $ZrO(NO_3)_2 \cdot xH_2O$ (16.66 gm, 0.0574 moles). After all three salts were dissolved into the water the pH was about 1. Concentrated $NH_4OH$ (39 ml) was added dropwise to the warm solution causing a white precipitate to form. At a pH of 6 the solution became more viscous. Continued addition of $NH_4OH$ brought the pH up to 10 after which the thickened slurry was evaporated to dryness using a vacuum oven. The dry powder was placed into a yttria stabilized zirconia crucible and calcined in air as follows: The sample was heated from 25° C. at 4° C./min to 400° C., held at that temperature for 1 hour and then heated at the rate of 2° C./min to 800° C. It was held at 800° C. for 5 hours and then cooled to 25° C. Hard, tan colored particles were collected from the crucible.

Results:

An increase in activity and a decrease in $C_{2+}$ selectivity was associated with an increase in the surface area of the contact material. The average pore radius steadily decreased as surface area increased. Also, combustion product selectivities (e.g., selectivities for CO and $CO_2$) increased with the higher surface area materials of the invention.

COMPARATIVE EXAMPLE 1

Catalyst of 1% $Sr/La_2O_3$

A catalyst of 1% Sr/$La_2O_3$ was prepared by an incipient wetness technique wherein an aqueous strontium nitrate was added dropwise to a dried $La_2O_3$ powder in the following manner:

An incipient wetness study showed that 0.478 grams of $H_2O$ was needed to impregnate 1.0 gram of $La_2O_3$ to incipient wetness.

A 2000.0 gram sample of $La_2O_3$, which had been calcined in flowing air at 500° C. for 2 hours, was impregnated to incipient wetness with 956 grams of water containing 48.31 grams of dissolved $Sr(NO_3)_2$. The resulting material was allowed to sit at room temperature for 2½ hours and then dried overnight at 250° F.

The dried material was spread thinly and calcined in flowing air at 1112° F. for 4 hours.

COMPARATIVE EXAMPLE 2

Catalyst of 1% Ba/$Y_2O_3$

A catalyst of 1% Ba/$Y_2O_3$ was prepared by adding an aqueous solution of barium nitrate dropwise to a $Y_2O_3$ powder. $Y_2O_3$, in an amount of 30 grams (0.1329 moles), was weighed into a beaker. $BaNO_3$, in an amount of 0.585 grams ($2.18 \times 10-3$ moles), was weighed into a beaker and dissolved in 20.4 ml of distilled water by gently heating the beaker containing the $BaNO_3$ and distilled water. This solution was then added dropwise to the beaker containing the $Y_2O_3$ and physically mixed with the $Y_2O_3$ by means of a magnetic stir bar to ensure homogeneous wetting of the $Y_2O_3$. After all of the solution had been added, the resulting slurry was transferred to a yttrium stabilized zirconia crucible and calcined in air as follows: The sample-containing crucible was placed in a programmable electric furnace and heated to 400° C. by increasing the temperature at the rate of 4° C./min, then maintained at 400° C. for 1 hour, followed by heating to 800° C. by increasing the temperature at the rate of 2° C./min, then maintained at 800° C. for 8 hours, and then finally cooled to room temperature.

COMPARATIVE EXAMPLE 3

Catalyst of 8% Ba/$Y_2O_3$

A catalyst of 8% Ba/$Y_2O_3$ was prepared by an incipient wetness technique wherein an aqueous solution of barium nitrate was added dropwise to a dried $Y_2O_3$ powder. $Y_2O_3$, in an amount of 30 grams (0.1329 moles), was weighed into a beaker and dried overnight in a vacuum oven at 140° C. $BaNO_3$, in an amount of 5.721 grams ($2.19 \times 10^{-2}$ moles), was weighed into a beaker and dissolved in 40 ml of distilled water by gently heating the beaker containing the $BaNO_3$ and distilled water. The $BaNO_3$ solution was added dropwise to the $Y_2O_3$ until the wetness point of the material was reached (i.e., after about 20 ml of the $BaNO_3$ solution had been added) forming a slurry. The slurry was gently heated to dryness and then the balance of the $BaNO_3$ solution was added dropwise to the dried material. After all the solution had been added, the resulting slurry was transferred to a yttrium stabilized zirconia crucible and calcined in air as follows: The sample-containing crucible was placed in a programmable electric furnace and heated to 400° C. by increasing the temperature at the rate of 4° C./min, then maintained at 400° C. for 1 hour, followed by heating to 900° C. by increasing the temperature at the rate of 2° C./min, then maintained at 900° C. for 8 hours, and then finally cooled to room temperature.

The final material was subjected to XRF analysis and found to contain 8% Ba.

EXAMPLE 14 AND COMPARATIVE EXAMPLES 4, 5 AND 6

Lifetime testing

The $YBa_2Zr_3O_x$ contact material composition of Example 1 and the catalysts of 1% Sr/$La_2O_3$ (Comparative Example 1), 1% Ba/$Y_2O_3$ (Comparative Example 2), and 8% Ba/$Y_2O_3$ (Comparative Example 3), respectively, were tested in a fully automated plug flow microreactor, which utilized a SETCON program to control all reactor heating cycles, gas flows and valve switching. In addition, all the contact material samples in the reactor were diluted with alpha-alumina to permit better heat control, in the ratio of 7 parts diluent per 1 part of contact material.

A gas feedstock containing 30% $CH_4$, 6% $O_2$ with the balance being $N_2$ was used. Reaction conditions included a reaction temperature of 850° C. and, as operation at or near 100% $O_2$ conversion was desired, the feed rate (325 ml/min) was selected to obtain 100% oxygen conversion at the start of the run. (Note: In view of the high cost of pure $O_2$, maximizing the utilization of $O_2$ is generally preferred.)

Results

FIGS. 7 and 8 show the effect on $C_{2+}$ selectivity and oxygen conversion, respectively, with time obtained in Example 14 and Comparative Examples 4, 5 and 6.

For both $C_{2+}$ selectivity and oxygen conversion, the largest declines over time were realized with the 1% Sr/$La_2O_3$ catalyst of Comparative Example 1. The 1% Ba/$Y_2O_3$ catalyst of Comparative Example 2 and the 8% Ba/$Y_2O_3$ catalyst of Comparative Example 3 realized the next greatest deactivation rates. The $YBa_2Zr_3O_x$ contact material composition of Example 1 realized the lowest deactivation rate of these tested materials.

EXAMPLES 15 AND 16 AND COMPARATIVE EXAMPLES 7, 8 AND 9 AND 10, 11 AND 12

Metal leeching rate testing

The $YBa_2Zr_3O_x$ contact material composition of Example 1 and the catalysts of Comparative Examples 1, 2 and 3, respectively, were subjected to bulk metals analysis by X-ray fluorescence in Example 15 and Comparative Examples 7, 8 and 9, respectively.

In addition, after a time on stream of 120 hours, the contact material used in Example 13 and the catalysts used in Comparative Examples 4, 5 and 6, respectively, were also subjected to bulk metals analysis by X-ray fluorescence in Example 16 and Comparative Examples 10, 11 and 12, respectively.

Results

Table 5 shows the bulk metal analysis results obtained.

In comparing the used with the fresh materials, 1% Sr/$La_2O_3$ had lost virtually all of the Sr with 120 hours on stream. 1% Ba/$Y_2O_3$ had lost over 70% of the Ba with 120 hours on stream. 8% Ba/$Y_2O_3$ had lost about 12% of the Ba with 120 hours on stream. $YBa_2Zr_3O_x$ lost virtually no Ba, Y or Zr with 120 hours on stream under the same reaction conditions.

These examples show that the compositions of the subject invention, even when subjected to the extreme reaction conditions associated with oxidative coupling are not subject to the high rates of volatilization associated with other contact material compositions. This translates into an increased lifetime for the contact material composition, as compared to known oxidative coupling contact materials which undergo substantial metal lose with time on stream.

TABLE 5

| Bulk XRF Analysis | | | | |
|---|---|---|---|---|
| | | Sr (Wt. %) | La (Wt. %) | |
| Comp. Ex. 7 | Fresh | 0.98 | 81.5 | |
| Comp. Ex. 10 | Used (120 hr) | 0.005 | 57.8 | |
| | | Ba (Wt. %) | Y (Wt. %) | |
| Comp. Ex. 8 | Fresh | 1.07 | 74.1 | |
| Comp. Ex. 11 | Used (120 hr) | 0.3 | 70.7 | |
| Comp. Ex. 9 | Fresh | 7.5 | 66.8 | |
| Comp. Ex. 12 | Used (120 hr) | 6.7 | 68.9 | |
| | | Ba (Wt. %) | Y (Wt. %) | Zr (Wt. %) |
| Ex. 10 | Fresh | 32.1 | 8.0 | 31.1 |
| Ex. 11 | Used (120 hr) | 32.0 | 8.4 | 40.7 |

The foregoing detailed description is given for clearness of understanding only, and no unnecessary limitations are to be understood therefrom, as modifications within the scope of the invention will be obvious to those skilled in the art.

That which is claimed is:

1. A composition which consists essentially of an intimately mixed, mixed oxide of:
   (a) at least one cationic species of a naturally occurring Group IIIB element;
   (b) at least one Group IIA metal cationic species selected from the group consisting magnesium, calcium, strontium and barium; and
   (c) at least one additional metal cationic species selected from the group consisting of zirconium and hafnium.
2. The composition of claim 1 wherein the Group IIIB element is selected from the group consisting of yttrium, lanthanum, neodymium, samarium and ytterbium.
3. The composition of claim 2 wherein the Group IIIB element is yttrium.
4. The composition of claim 1 wherein the Group IIA metal is strontium.
5. The composition of claim 1 wherein the Group IIA metal is barium.
6. The composition of claim 1 wherein the additional metal is zirconium.
7. The composition of claim 1 wherein the additional metal is hafnium.
8. The composition of claim 1 wherein the contact material comprises in the range of about 10 to 55 wt. % of the additional metal, on an elemental basis.
9. The composition of claim 1 wherein the Group IIIB element cationic species and the Group IIA metal cationic species are present in an approximate molar ratio of about 1 Group IIIB element cationic species to about 0.5 to 3 Group IIA metal cationic species.
10. The composition of claim 9 wherein the Group IIIB element cationic species and the Group IIA metal cationic species are present in an approximate molar ratio of about 1 Group IIIB element cationic species to about 1.5 to 2.5 Group IIA metal cationic species.
11. The composition of claim 1 wherein the contact material is represented by the formula:

$$Y_xBa_{(1-x)}ZrO_{(3+x/2)}$$

wherein $0<x<1$.

12. The composition of claim 11 wherein $0.3<x<0.7$.
13. The composition of claim 1 wherein the contact material has a surface area in the range of about 0.1 m²/g to about 100 m²/g.
14. The composition of claim 13 wherein the contact material has a surface area of about 1 m²/g to about 10 m²/g.

* * * * *

UNITED STATES PATENT AND TRADEMARK OFFICE
CERTIFICATE OF CORRECTION

PATENT NO. : 5,312,795
DATED : May 17, 1994
INVENTOR(S) : Mark P. Kaminsky; Mark S. Kleefisch; George A. Huff, Jr.; Don M. Washecheck; Mark K. Barr.

It is certified that error appears in the above-indentified patent and that said Letters Patent is hereby corrected as shown below:

| Col. | Line | |
|---|---|---|
| 11 | 53 | "of about 1 Group IIB element" should read -- of about 1 Group IIIB element -- |
| 11 | 58 | "as Group IIB elements" should read -- as Group IIIB elements" -- |

Signed and Sealed this

Twenty-third Day of August, 1994

Attest:

BRUCE LEHMAN

Attesting Officer

Commissioner of Patents and Trademarks